(12) United States Patent
Goroshevskiy et al.

(10) Patent No.: US 8,949,042 B1
(45) Date of Patent: Feb. 3, 2015

(54) AUV PIPELINE INSPECTION USING MAGNETIC TOMOGRAPHY

(71) Applicants: Valerian Goroshevskiy, Moscow (RU); Svetlana Kamaeva, Moscow (RU); Igor Kolesnikov, Moscow (RU); Leonid Ivlev, Moscow (RU)

(72) Inventors: Valerian Goroshevskiy, Moscow (RU); Svetlana Kamaeva, Moscow (RU); Igor Kolesnikov, Moscow (RU); Leonid Ivlev, Moscow (RU)

( * ) Notice: Subject to any disclaimer, the term of this patent is extended or adjusted under 35 U.S.C. 154(b) by 0 days.

(21) Appl. No.: 14/242,938

(22) Filed: Apr. 2, 2014

(51) Int. Cl.
*G01N 27/82* (2006.01)
*G01V 3/08* (2006.01)

(52) U.S. Cl.
CPC ................ *G01N 27/82* (2013.01); *G01V 3/087* (2013.01)
USPC ............................................... 702/38; 702/36

(58) Field of Classification Search
CPC ... G01N 29/2412; G01N 27/82; G01N 27/85; G01L 1/12; G01L 3/102; G01V 3/087; G01B 7/24
USPC ............................................... 702/35, 36, 38
See application file for complete search history.

(56) References Cited

U.S. PATENT DOCUMENTS

| | | | | |
|---|---|---|---|---|
| 4,072,200 | A * | 2/1978 | Morris et al. | 175/45 |
| 4,727,360 | A * | 2/1988 | Ferguson et al. | 340/572.2 |
| 6,424,150 | B2 * | 7/2002 | Kwun et al. | 324/216 |
| 2003/0167998 | A1* | 9/2003 | Huntsman | 114/312 |
| 2013/0027029 | A1* | 1/2013 | Goroshevskiy et al. | 324/228 |
| 2014/0097835 | A1* | 4/2014 | Sartee et al. | 324/251 |

FOREIGN PATENT DOCUMENTS

WO   WO 0000848 A1 * 1/2000

OTHER PUBLICATIONS

Kwun, Hegeon. "Back in Style: Magnetostrictive Sensors," Technology Today, Fall 1991, Southwest Research Institute. [retrieved on Jun. 11, 2014] Retrieved from the Internet: <URL:http://www.swri.org/3pubs/ttoday/fall91/magneto/magneto.htm>.*
Remotely Operated Vehicle Committee of the Marine Technology Society, "ROV, AUV, and AUV/ROV Hybrid Manfacturers, Operators, Subsystems, and Related Industries," Nov. 2, 2012. [retrieved on Jun. 11, 2014] Retrieved from Internet: <URL:http://web.archive.org/web/20121102120428/http://www.rov.org/industry_all.cfm>.*

* cited by examiner

*Primary Examiner* — Jonathan C Teixeira Moffat
*Assistant Examiner* — Liam R Casey
(74) *Attorney, Agent, or Firm* — Nadya Reingand; Yan B. Hankin

(57) ABSTRACT

The present invention discloses an autonomous magnetic tomography method (MTM) and device for magnetographic identification and magnetographic analysis of mechanical flaws and defects along structures located deep in the sea or otherwise located underwater and further underground. The invention optimizes the inspection and maintenance processes of extended metallic constructions, e.g., pipelines. The device is based on the inverse magnetostrictive effect (i.e., the Villari effect)—the variation of a material's magnetic susceptibility under applied mechanical stress. The changes in magnetic susceptibility result in distribution of a magnetic field gradient along a structure's surface area, thus providing information about the presence and the value of the magnetic field anomaly at a given and precise location on the structure. The device and method is capable of autonomous and offline operation underwater at depths up to 1,500 meters below sea level.

18 Claims, 4 Drawing Sheets

US 8,949,042 B1

AUV PIPELINE INSPECTION USING MAGNETIC TOMOGRAPHY

CROSS-REFERENCE TO RELATED APPLICATIONS

This application is a continuation-in-part of U.S. patent application Ser. No. 13/662,427, filed Oct. 27, 2012; now U.S. Pat. No. 8,447,532; and U.S. patent application Ser. No. 13/674,118 filed Nov. 12, 2012; now U.S. Pat. No. 8,542,127. This application claims priority to, and incorporate fully by reference, said Patent application, as well as U.S. Provisional Patent application No. 61/807,378, filed Apr. 2, 2013.

FIELD OF THE INVENTION

This invention relates to underwater measurements, and particularly to pipeline inspection using an autonomous underwater vehicle (AUV) for monitoring of subsea structures and facilitating inspection or other operations performed on or near the structures. The invention further relates to surveying the condition of underwater structures, performing periodic, repairs, and performing maintenance on said structures.

BACKGROUND OF THE INVENTION

The major causes of pipeline failures around the world are external interference and corrosion; therefore, assessment methods are needed to determine the severity of such defects when they are detected in pipelines. Pipeline integrity management is the general term given to all efforts (design, construction, operation, maintenance, etc.) directed towards ensuring continuing pipeline integrity.

When carrying out an inspection, all prior art AUVs (autonomous underwater vehicles) must be designed to follow an appropriate subsea structure within a close proximity in order to provide useful and accurate information. Typically, AUVs carry various types of equipment to form images of a surveyed underwater structure. Such equipment typically implements either a sonar technology or visual imaging. AUVs can normally follow the structure autonomously, without any needed help from an external operator.

The present invention addresses prior art problems including, but not limited to, (1) sensor positioning, and (2) AUV operation control, during underwater pipeline inspection.

SUMMARY OF THE INVENTION

An autonomously driven device comprising at least one set of magnetic tomography sensors is disclosed. The device is intended for use in a subsea environment to inspect pipelines and other structures located as deep as 1.5 kilometers below sea level. The device comprises an independent power supply, three or more sensors for registering magnetic tomography signals caused by the Earth's magnetic field interacting with defects along a pipeline (known as the Villari effect), a processing unit, and a tracking mechanism. The sensors are arranged in such a way as to avoid overlapping or shadowing if and when the device turns about its axis, and in order to obtain the most accurate reading. The processing unit converts the registered sensor data into a defect distribution map which details the precise 3-D location of defects along the pipeline and the risk associated with each defect.

DETAILED DESCRIPTION OF THE PREFERRED EMBODIMENT

Definitions

Figure 1:
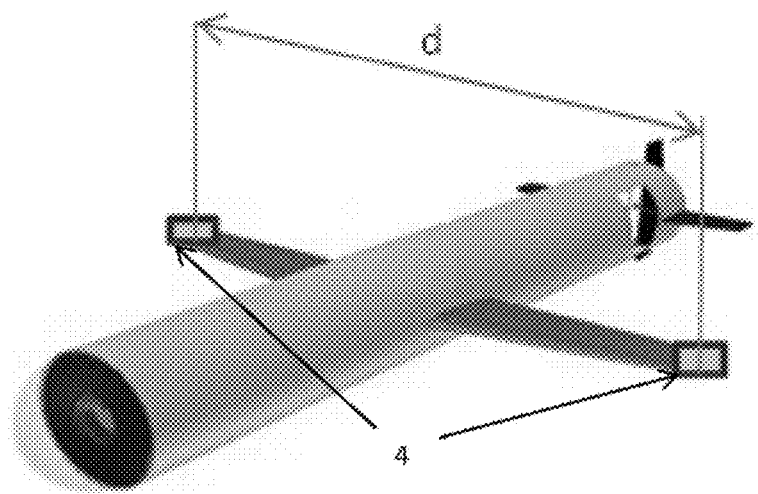
FIG. 1 illustrates an example of prior art comprising two MTM sensors.

The term "remote," as used herein is defined as being used from a substantial distance from a structure under testing. The term is used to signify that a sensor, as defined herein, is not necessarily located in close proximity to the structure being tested. The preferred embodiment of the invention performs best when the distance between structure and sensors ranges from 1-50 meters, however, the term remote is intended to mean up to 15 times the diameter of the structure being surveyed. This makes the invention especially effective for testing structures located deep underground and underwater.

The term "threshold distance," as used herein, is defined as an amount equal to 15 (fifteen) times the diameter of a structure being surveyed, or scanned. The term is used to describe the range of the device and method claimed herein (i.e. the maximum distance between a given structure and a device during operation).

The term "sensor," or "sensors," as used herein, is defined as an interconnected sensing unit. The term should be read as a sensing unit comprising three or more magnetic signal, or magnetic tomography (MTM) sensors, which detect the signal caused by the Earth's magnetic field after it travels through a structure being inspected. Such sensors also detect any artificial MTM signal by an additional MTM signal generator.

The term "memory unit," as used herein, is defined as a module which saves signals registered by the sensors or sensor array to a file as data. The memory unit acts as a step between the sensors and the processing unit.

The term "processing unit," as used herein, is defined as a module which receives MTM sensor data (potentially via a memory unit) and further processes the various files to determine (1) the presence of anomalies/defects along a structure, (2) the risk corresponding to each anomaly (e.g., the size/depth of the defect), (3) the three-dimensional location of each anomaly along a structure, and (4) whether the device is maintaining correct positioning, in tracking the structure.

The term "MTM," or "magnetic tomography method," as used herein, is defined as a non-contact pipeline surveying method employing detected differences in the magnetic field near a ferro-magnetic structure. The term "MTM sensor" refers the specific sensor(s) which detect the magnetic field created by (1) the Earth, or (2) the MTM signal generator. The term "MTM signal generator" refers to an additional emitter of an electromagnetic or magnetic signal.

The term "second signal generator," as used herein, is defined as any additional signal emitter according to known methods in the art. Similarly, the term "second sensing unit" is defined as any additional sensing mechanism according to known methods in the art. The second signal generator and second sensing unit are part of a mechanism of tracking the axis of an underwater structure to ensure that the device is operating along the correct path.

The term "horizontal cross section," as used herein, is defined as the cross section of the body of a device as claimed herein corresponding to a slice perpendicular to the trajectory of the device. For example, if the device were in the shape of a cylinder, a horizontal cross section corresponds to the shape of a circle (and not a rectangle, which would correspond to a vertical cross section of the same cylinder).

The term "odometer," as used herein, is defined as a portable odometer unit, fixable to a main unit (i.e. the apparatus), intended for distance measurement along a route of extended engineering structure such as a pipeline. The odometer facilitates fixing of the linear coordinates of defect areas revealed during in-line, non-contact magnetometric or other diagnostic inspection. The odometer can be used for marking the longitudinal coordinates along, an underwater structure axis for compilation of data for a database for certification of each process, and as a unit of a pipeline route-tracer set with a function of laying depth measurement.

The present invention discloses an autonomous magnetic tomography method (MTM) and device for magnetographic identification and magnetographic analysis of mechanical flaws and defects along structures located deep in the sea or otherwise located underground and/or underwater. The invention optimizes the inspection and maintenance processes of extended metallic constructions, e.g., pipelines.

The MTM device is based on the inverse magnetostrictive effect (i.e., the Villari effect)—the variation of a material's magnetic susceptibility under applied mechanical stress. Generally, this technique uses the natural magnetization of a ferrous pipe by the Earth's magnetic field. The changes in magnetic susceptibility result in distribution of a magnetic field gradient along a structure's surface area, thus providing information about (1) the presence, and 2) the value of the magnetic field anomaly at a given and precise location on the structure. In this invention, the device is capable of autonomous and offline operation underwater at depths up to 1,500 meters below sea level.

The device and method disclosed comprise various types of sensor positioning. Some examples are provided below.

One embodiment of the present invention comprises a system of pairs of sensors registering MTM signals for MTM inspection of a structure. According to the prior art, MTM sensors 4 can be positioned and paired in a planar manner (see FIG. 1), where the distance d between the sensors 4 is selected based on the requirements of particular MTM specifications (see, e.g., U.S. patent application Ser. No. 13/662,427). The present invention suggests that the number of sets of planar remote sensor arrays should be more than one (e.g., two, three, four, and so on), and in such an embodiment, preferably at least three (see FIG. 2). This results in a 2-dimensional manner of positioned the sensors. In this case, two or more sections perform measurement at the same time, thus simultaneously providing individual longitudinal magnetic field gradients. With 2-dimensional positioning of MTM sensors, the distance between the sensors d is pre-calculated so that data registered by the sensors can be processed to form a map of the surveyed structure.

Figure 6:
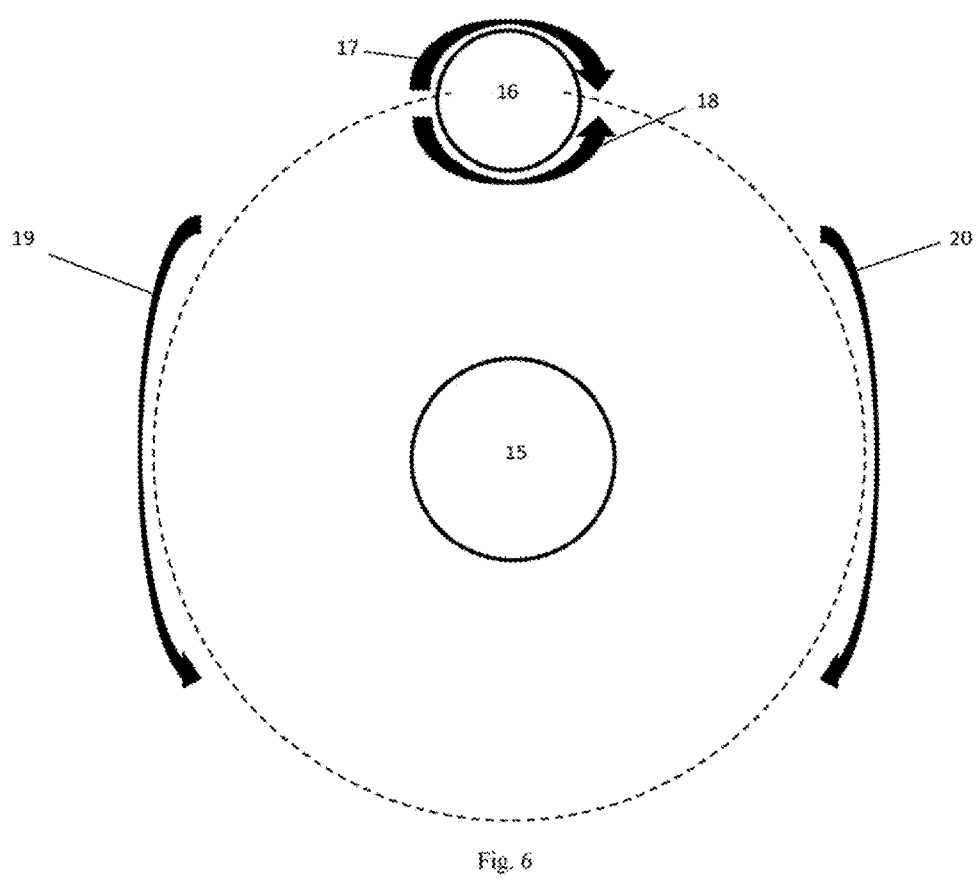
FIG. 6 shows an example of the device's rotation about its own axis and about the axis of the surveyed structure.

In some embodiments based on a 2-dimensional positioning of MTM sensors, the body of the device rotates as the scanning occurs (see FIG. 6). Thus, the MTM sensors coupled to the device turn in a spiral manner about the lengthwise axis that the device follows during scanning due to the rotation by the device. The device 16 can rotate in either direction about its long axis (e.g., clockwise and counter-clockwise) 17, 18. This allows the MTM sensors to register signals while turning about an axis, in order to determine the exact locations of defects when anomalies are noted. This rotation increases the accuracy of the results obtained by continuously changing the position of the sensors involved. It should be noted that such rotation is not limited to those embodiment with a 2-dimensional positioning of MTM sensors, and the same can occur in all other embodiments with all other types of sensor positioning (e.g., 3-dimensional, etc.). The rotation especially enhances the data obtained with regard to the 3-D mapping ability of the device (by rotating rather than remaining stationary during, scanning, the MTM sensors are able to scan every portion of the underwater structure (e.g. the top, bottom, sides, and everything in between). Additionally, and in other embodiments, the device 16 is able to rotate about the axis of the underwater structure 15 rather than its own axis. Again, the device can rotate in either direction (e.g., clockwise and counter-clockwise) 19, 20. This type of rotation also increases the accuracy of information obtained, by positioning the MTM sensors at various locations about the structure (e.g., above, below, along the sides, and everywhere in between). It is additionally noted that the device can perform both such rotations at any given distance from the structure as long as it is within the threshold distance.

Situations may arise where it is impossible to provide a predetermined distance between the sensors (due to, e.g., a limitation of the dynamic characteristics of an AUV). Under such circumstances, the number of sensors 4 is varied and the sensors are positioned in an axial manner (i.e. along the surface of the device), wherein the sensors may be arranged at equal distances from a central point or at equal distances relative to each other. In the preferred embodiment, the sensors are arranged axially at equal angles relative to each other from a center point of the device (e.g. 3 sensors arranged at 120 degrees relative to one another from a center point). An example of this embodiment is shown in FIGS. 4B (showing 8 axially arranged sensors) and 4C (showing 3 axially arranged sensors). The sensors are coupled either to the outer surface of an AUV device 5 (FIG. 3B, showing 8 sensors), or to the inside surface of the AUV device 6 (FIG. 3C, showing 3 sensors). Multiple sets 3 of axial sensors may be installed on the AUV device, as shown in FIG. 3A (preferably, each set of sensors comprises a number of sensors in multiples of 3, i.e., 3, 6, 9, 12, and so on). The distance $d_1, d_2, d_3, \ldots$ between each sets of sensors 3 and the MTM signal generator 2 is pre-calculated in order to most accurately display the MTM information and decrease any interference noise.

Figure 2:
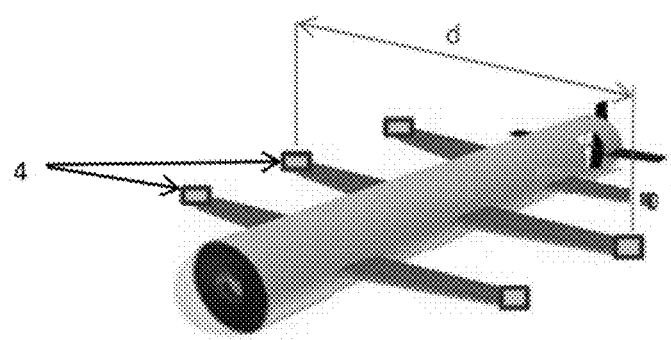
FIG. 2 shows a simple improvement upon the prior art shown in FIG. 1. In this example, the presently claimed device is coupled to three pairs of MTM sensors positioned in a 2-dimensional manner.
Figure 3:
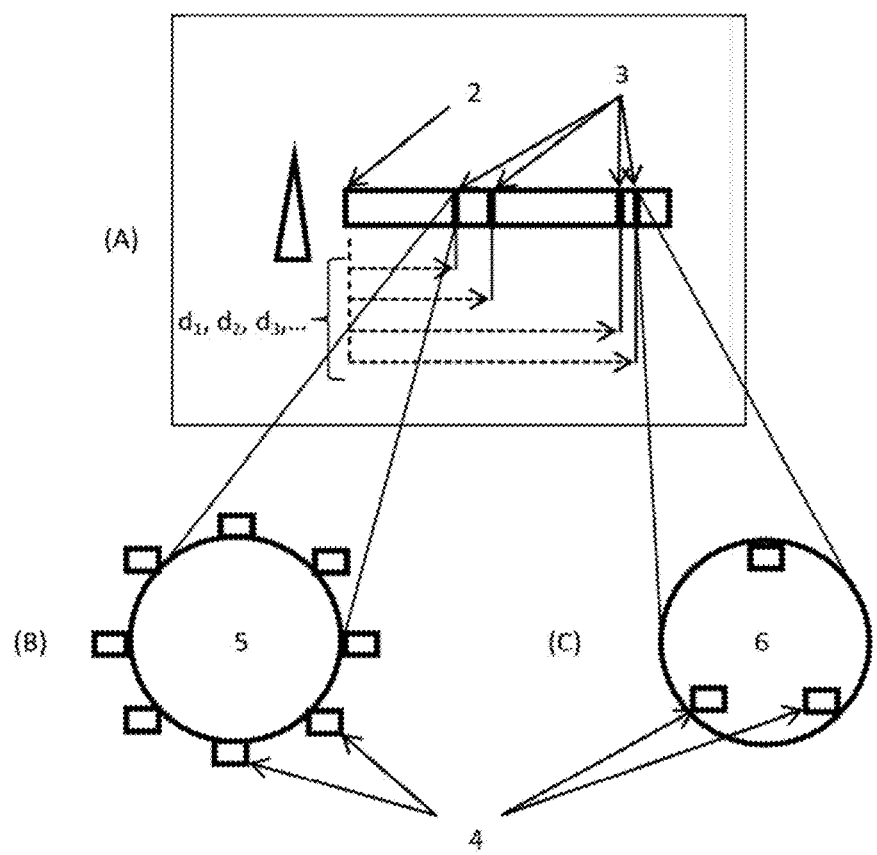
FIG. 3A shows an example of a device, showing cross-sections of sensors and the predetermined distances between a MTM signal generator and the sensors.
FIG. 3B shows an example of 8 sensors positioned axially along a device's outer surface.
FIG. 3C shows an example of 3 sensors positioned axially along a device's inside surface.
Figure 5:
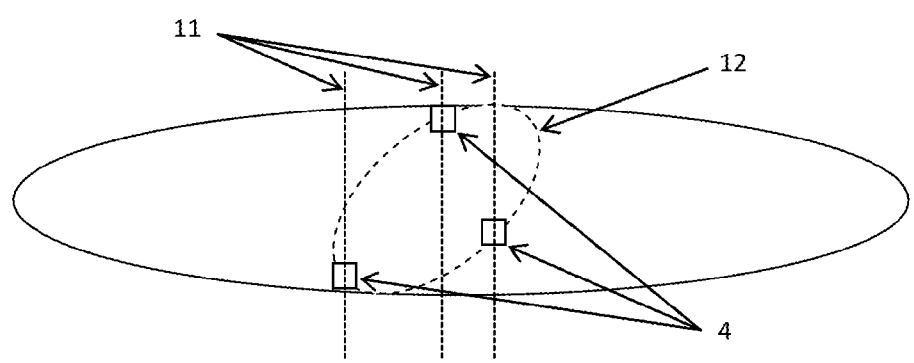
FIG. 5 shows an example of how three sensors can be positioned at various horizontal cross sections of the device (i.e., in a 3-dimensional manner).

FIG. 1 shows an example of prior art, where two sensors 4 are coupled, in pairs and with a known distance between each other d, to an AUV device, and the sensors 4 are located on the same plane relative to each other. FIG. 2 illustrates an example of how the present invention improves upon the prior art—by increasing the number of sensors and placing them on separate planes relative to each other. FIG. 2 exemplifies a 2-dimensional manner of positioning the MTM sensors according to the present invention. FIG. 3 exemplifies another embodiment of the present invention, where MTM sensors 4 are placed along the outer surface 5 or the inner surface 6 of the device (i.e., axially) in order to obtain more accurate information. FIG. 3 further shows bow the MTM sensor arrays 3 can comprise various numbers of MTM sensors 4. FIG. 3 shows, e.g., four horizontal cross sections of MTM sensor arrays 3, with two of these arrays 5, 6 being further detailed. Although not required, it is preferable that the MTM sensors be positioned such that at least three (i.e. three or more) MTM sensors lie on a separate horizontal cross section of the device. For example, three (or more) sensors can lie on an angular cross section (see FIG. 5), FIG. 5 illustrates an example of a 3-dimensional manner of positioning the MTM sensors: Three MTM sensors 4 are positioned axially on the device such that each sensor 4 is on a separate horizontal cross section 11; thus, together, the sensors lie on an angular (or 3-dimensional) cross section 12 of the device. 3-dimensional positioning avoids the problem of the device twisting or rotating during scanning potentially causing MTM sensors to overlap or shadow one another.

Figure 4:
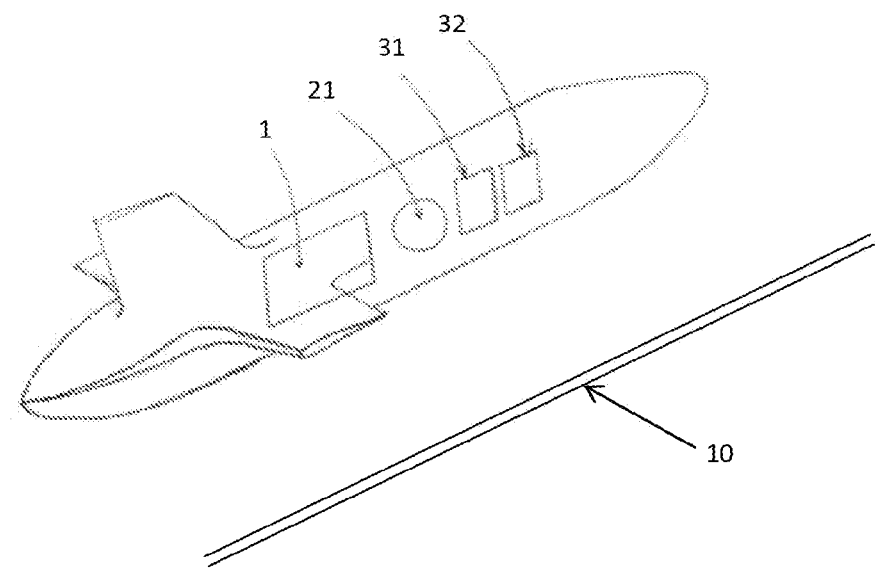
FIG. 4 shows an example of a means for tracking the axis and course of a structure as described herein.

FIG. 4 illustrates another embodiment of the present invention, comprising an additional feature of tracking the underwater structure 10 as it is surveyed. Interconnected units are located internally within the AUV device, or alternatively as part of a different AUV. The units that comprise this additional feature include, but are not limited to, a power supply 1, a second signal generator unit 21 comprising (1) a second signal emitter (not limited to MTM signals, can be any known underwater signaling method) and (2) an electric module for signal processing, as well as a second sensing unit comprising two separate sensors: (1) a sensor for determining the path and direction of the underwater structure 31, and (2) a sensor for determining the distance from the structure 32. Such course tracking stabilization is a potential additional feature of the present invention. This embodiment is capable of tracing the axis of an underwater (including sub-silt, sub-bed, and saltwater) metallic (including non-ferromagnetic) current-conducting object, including, but not limited to, pipelines and cables. The active electromagnetic emitter of the second signal generator unit 21 may be mounted, for example; on an AUV or ROV frame, or on a separate carrier, or may be installed or stationary. The additional sensors 31, 32 (e.g., coils with shafts), are positioned far enough away from the signal emitter 21 (the distance depends on the physical dimensions of the AUV or ROV, where providing a large distance between the emitter 21 and the sensors 31, 32 provides for natural diminishing of a direct signal from the emitter 21). The electronic module for signal processing removes the direct influence from the emitter that is present due to the proximity of the second signal emitter to the sensors. The sensors must be able to register only the induced signal that comes from the underwater structure being surveyed. Direct signal elimination provides possibilities for AUV (ROV) automatic or semi-automatic search for the surveyed structure and course stabilization along its axis. Direct signal elimination is achieved by this electronic module via special processing of received signals taking into account the relative positions of all second sensors and the second signal emitter. A non-contact coil-based second signal emitter is used to induce low-frequency current in the current-conducting surveyed structure. A circular magnetic field, generated by the low-frequency currents induced in the structure, is detected by the second sensors, which are placed at a distance from the emitter. The signals from the sensors are processed by a customized processing system which determines a signal to noise ratio in the following manner: the specialized signal emitted by the second signal generator unit is treated as "noise," while the induced conductivity causing the magnetic field in the structure is treated as "signal."

The array of remote MTM sensors coupled to the device according to the present invention is capable of localizing coordinates of an underwater structure at any given moment and detecting anomalies of the magnetic field at each localized coordinate along a structure, thus employing a non-contact remote technique based on measuring a value of the Earth's magnetic field at various locations as the device approaches, reaches, and departs from a specific area of the structure. It should be noted that the array of sensors is capable of obtaining 3-dimensional information such that the processing unit can create a 3-dimensional defect distribution map. That is, the device is able to determine the precise location of a defect at a specific area of a surveyed structure (e.g., on the bottom, on left side, on the right side, on the top, etc.).

The remote sensors register information which makes it possible to identify anomalies on and along a structure by measuring the deviation of the Earth's magnetic field at each monitoring location from a control, or background, value, without the need for an additional magnetic field or signal during the measuring process. It is noted, however, that certain embodiments of the present invention do comprise an additional MTM signal generator for signal amplification purposes (see further below).

The remote sensor array is further capable of localizing coordinates of foreign objects in the vicinity of a structure, processing anomaly locations with such foreign objects, and making and recording a link between the anomaly location and a nearby foreign object and its location.

The use of the AUV device claimed herein doesn't require any preparation of the pipeline for testing, e.g., cleaning, opening the pipe, or stopping pipeline operation. The device is capable of detecting flaws of various types, including but not limited to internal or external corrosion, long crack-like pipeline defects, and welding defects. The use of the device is not limited by features such as a structure's diameter, configuration, or protective coatings, change of pipe diameter or wall-thickness, turning or twisting pipes, transported product within the pipe (e.g., gas, oil, water), pressure, and pipeline protection (e.g., cathodic protection).

The claimed device evaluates the degree of danger of defects by the level of concentration of mechanical tensions (instead of e.g., defect geometry (i.e., length-width-depth)).

The claimed method and device are able to scan structures from a distance of up to 15 times the diameter of the surveyed structure ("threshold distance"). For example, if a pipe is one-half meter (0.5 m) in diameter, the claimed device is capable of obtaining detect information, using the same methods, at a distance of up to 7.5 meters from the structure. The device preferably should remain as close as possible, but generally, so long as the device is within the threshold distance, the medium (through which the magnetic and electromagnetic signals emitted and received must travel) is limited only by that through which such waves cannot travel. Thus, the claimed method and device is capable of scanning further below a seabed (i.e. through a sea bottom, because the transmitted waves are capable of penetrating the seabed) for structures so long as they are located within the threshold distance. This is particularly applicable for the scanning of structures which penetrate the seabed in certain areas, whose sections are not visible in those areas. The claimed device, however, can perform continuously without additional support even in such areas, due to the transmissibility through the ground of the signals emitted, received, and processed.

The claimed method and device optionally include an additional MTM signal generator 2 that produces specific and different signals relative to the Earth's natural magnetic signal. Such signals include but are not limited to those with specified/predetermined characteristics such as timing (e.g., one or more pulses of a signal), amplitude, phase, and frequency. This additional MTM signal can emitted in areas of high external noise and other interfering objects based on determinations made by the processing unit of the device. The processing unit analyzes the data registered by the MTM sensors for a variation (anomaly) from a predicted normal signal to determine the presence of a defect along the structure being surveyed (i.e., based on the change from a generated signal uniformity). The choice of the signal's characteristics is based on the particular pipeline or structure under investigation. This can be adjusted during preliminary testing in the lab or directly onsite.

The additional MTM signal is generated by a set of magnetic coils being oriented relative to each other in a specific way. Required output power is determined and provided by the power supply.

Several methods to generate additional signals are proposed by the present invention. Some examples are given here:

In one embodiment a unified signal is emitted, transmitted, and detected by all sensors. The distance from the generator to the sensors is taken into account. This type of signal permits the AUV unit to analyze the decay rate of the signal associated with the non homogeneity of a magnetic field line caused by defects inside, outside, or along a structure. This type of signal generation is more cost-effective with regard to power generation. This particular method allows for a more precise adjustment of sensors based on a single level of signal generation (i.e. one signal, rather than more than one), as the generated signal strengthens the (electro)magnetic signal from the structure being scanned (e.g., in the case of a weak natural signal) and decreases the external noise of any potentially interfering objects.

In another embodiment, two or more signals are generated for each particular sensor. The characteristics of each signal generated must be identical to each other, and the distance from the generator to the sensors should be the same. This type of system may be preferable when stronger interference signals exist between a pipeline and third party objects, and/or when it is more difficult to extract a desired signal due to background noise.

Power supply system. The power supply system comprises two individual units:

A main power unit provides power for the AUV device. The AUV device powers the MTM signal generator. The power supply required for the performance of the AUV unit is calculated based on the total capacity of every component of the AUV unit.

A second unit, i.e. an independent power unit, is used to back up the main power unit and ensure the integrity of information recorded by the recording unit and the backup storage unit.

Recording and storage of information. A memory unit is designed for safe data storage obtained during the scanning and analyzing process performed by the AUV device. Recording is carried out either (1) by running the internal clock unit, or (2) by an odometer (which is either coupled to the AUV device or part of an external AUV device/unit). Additionally, information on the longitudinal and GPS coordinates is synchronized with sensor readings, all of which is recorded in a single data file.

Before each individual scan, a new holding data file is created by the device. During the scan, the holding data file is filled with information from the scan until the arrival of a subsequent pulse either (1) from an odometer or (2) from an internal clock.

The claimed device and method continuously records and stores information, further organizing it within an external drive. At shorter distances below sea level, a known communications system may also be provided (e.g., radio, optical, wireless), which allows for control by an operator, as well as a means for transfer of control between an operator (e.g., human) and the AUV device itself—for online, or autonomous, operation. The AUV device can, however, operate in a completely autonomous fashion, surveying structures at depths beyond those where any presently known communications system can reach. In such cases, the claimed device operates alone, collecting the required data while moving along the structure, subsequently returning to the surface or at least a location where communication is once again possible.

The communication system provides the AUV device a connection with additional hardware and software for device operation and maintenance. Such additional hardware and software can be used for, e.g., additional power supply and/or regulation thereof, or a logical and physical interface other on-board systems of the device. A variety of known approaches can be used for an interface and the packet structure transmission and reception (e.g., RS-232, RS-485, Ethernet, CAN, file system and database structure, and DC/AC power).

Monitoring AUV device performance. A monitoring unit is designed to assess MTM system performance during scanning. The following factors, for example, are monitored: power level; sensor signals; the longitudinal coordinates of the device; the GPS coordinates of the device, and requirements of the communication system.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A remote device for integrity management of a surveyed underwater structure, comprising:
an independently powered body for moving underwater in an autonomous manner, at least three Magnetic Tomography Method (MTM) sensors, said sensors registering MTM signals, said registering being based on the Villari effect, said signals occurring continuously and naturally as a result of the Earth's magnetic field, transmitting through said structure, and being continuously received by each MTM sensor as said device nears, reaches, and departs from every point of said structure, wherein said at least three MTM sensors are positioned such that at least three MTM sensors lie on at least two separate horizontal cross sections of said body of the device, wherein those sensors which lie on one horizontal cross section are equally distant from all other sensors lying on the same horizontal cross section, and wherein at least one horizontal cross section comprises at least three sensors, a processing unit for receiving and interpreting said signals from said sensors, said processing unit converting the signals received and mapping a defect distribution along a length of said structure, and a means for tracking a location of a mapped defect, thus providing offline monitoring and risk evaluation of said structure.

2. The device of claim 1, further comprising a MTM signal generator, said generator emitting one or more timed MTM signal which transmits through the surveyed structure and is received by said MTM sensors, said MTM signal generator adding to said Earth's magnetic field and amplifying a signal of magnetic waves transmitted through the surveyed structure.

3. The device of claim 2, wherein said one or more timed MTM signal is a pulse signal and each of said at least three sensors is positioned at a predetermined distance from said MTM signal generator, and a timing of a signal return after reflection from the structure is used in the signal processing unit for defects distribution mapping.

4. The device of claim 2, wherein said processing unit further maps a 3-dimensional defect distribution of said structure.

5. The device of claim 2, wherein the device operates at a distance of up to 15 times the diameter of the structure.

6. The device of claim 2, further comprising a memory unit for organizing and storing received signals to a holding data file corresponding to a particular location of the structure, said holding data file storing all signals collected at said location.

7. The device of claim 2, wherein said means for tracking a location of a mapped defect comprises a computer which traces a linear coordinate along the structure and a time of signal reception.

8. The device of claim 2, wherein said processing unit further comprises a monitoring unit for assessment of device performance.

9. The device of claim 2, wherein said means for tracking a location of a mapped defect comprises an internal clock.

10. The device of claim 2, further comprising a GPS system to track an initial position of the device.

11. The device of claim 2, wherein said means for tracking a location further comprises an odometer.

12. The device of claim 2, wherein said independently powered body comprises a main power unit and a backup power unit.

13. The device of claim 2, further comprising a means for structure tracking comprising a second signal generator and a second sensing unit, said second signal generator emitting a signal that is reflected from the structure and received by said second sensing unit, thus determining an axis of the structure.

14. The device of claim 2, wherein said at least three sensors are positioned axially along an outside surface of the device.

15. The device of claim 2, wherein said at least three sensors are positioned axially along an inside surface of the device.

16. The device of claim 2, wherein said device is capable of monitoring a structure located up to 1,500 meters below sea level.

17. A method for integrity management of an underwater structure, comprising:

deploying an autonomous underwater device coupled with at least three Magnetic Tomography Method (MTM) sensors, wherein said MTM sensors are positioned such that at least three sensors lie on at least three separate horizontal cross sections of said body of the device, wherein each sensor which lies on one horizontal cross section is equally distant from all other sensors lying on the same horizontal cross section, and wherein at least one horizontal cross section comprises at least three sensors, registering, via said at least three sensors, MTM signals from Earth's magnetic field as said device moves along the underwater structure, wherein said MTM signals have travelled through said underwater structure, producing a Villari effect, registering a plurality of signals as said device nears, reaches, and departs from every point of said structure, converting said plurality, of MTM signals into data, and mapping a defect distribution along a length of said structure.

18. The method of claim 16, further comprising emitting one or more timed MTM signals via a MTM signal generator to amplify the Villari effect in areas with a high noise amount, and receiving said one or more timed MTM signals via said sensors after said one or more timed MTM signals has travelled through said underwater structure, thus improving said mapping of a defect distribution.

\* \* \* \* \*